US00PP35907P2

(12) United States Plant Patent
Knapp et al.

(10) Patent No.: US PP35,907 P2
(45) Date of Patent: Jul. 2, 2024

(54) STRAWBERRY PLANT NAMED 'UC KEYSTONE'

(50) Latin Name: ***Fragaria* x *ananassa* Duchesne**
Varietal Denomination: UC Keystone

(71) Applicant: The Regents of the University of California, Oakland, CA (US)

(72) Inventors: Steven J. Knapp, Davis, CA (US); Glenn S. Cole, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 18/135,708

(22) Filed: Apr. 17, 2023

(51) Int. Cl.
*A01H 5/08* (2018.01)
*A01H 6/74* (2018.01)

(52) U.S. Cl.
USPC ..... Plt./209
CPC ..... *A01H 6/7409* (2018.05)

(58) Field of Classification Search
USPC ..... Plt./209
CPC ..... A01H 6/7409; A01H 5/08
See application file for complete search history.

(56) References Cited

PUBLICATIONS

See information in accompanying Information Disclosure Statement letter.
Cal Poly Strawberry Center 2022 Strawberry Field Day, retrieved online at https://content-calpoly-edu.s3.amazonaws.com/strawberry/1/images/2022FieldDayBooklet-FINAL-07_22_22-PM-comp.pdf, 6 introductory pages, pp. 20-29. (Year: 2022).
U.S. Appl. No. 18/135,705, Non-Final Office Action dated Aug. 29, 2023, 9 pages.

*Primary Examiner* — Keith O. Robinson
(74) *Attorney, Agent, or Firm* — Kilpatrick Townsend & Stockton LLP

(57) ABSTRACT

'UC Keystone' is a 'day-neutral' flowering cultivar of a strawberry plant that produces exceptionally high yields of firm, long shelf-life fruit and is resistant to *Fusarium* wilt, *Verticillium* wilt, and *Phytophthora* crown rot.

2 Drawing Sheets

Genus and species: The strawberry plant of this invention is botanically known as *Fragaria* x *ananassa* Duchesne.

Variety denomination: The variety denomination is 'UC Keystone'.

BACKGROUND

This invention relates to a new and distinct day-neutral strawberry cultivar designated as 'UC Keystone', which originated from a cross performed in the winter of 2017. The plant of this selection was originally designated '17C138P062'.

BRIEF SUMMARY

'UC Keystone' is a *Fusarium* wilt resistant day-neutral cultivar that originated in the winter of 2017 from a cross between 'UCD Moxie' (U.S. Plant Pat. No. 32,953) and 'UCD Warrior' (U.S. Plant Pat. No. 32,950). It is not known which is the male parent and which is the female parent. Clones of 'UC Keystone' were initially propagated from a single mother plant in 2018. 'UC Keystone' has since been preserved by annual cycles of asexual propagation from stolons in a facility at Winters, California.

'UC Keystone' was selected from a full-sib family (17C138) generated from the cross between 'UCD Moxie' and 'UCD Warrior'. 'UC Keystone' shares one of the same parents, 'UCD Moxie', with 'UC Golden Gate' (U.S. Plant patent application Ser. No. 18/135,710, filed of even date). Seeds of the 17C138 family and the full-sib family 17C139, from which 'UC Golden Gate' originated, were harvested from greenhouse-grown plants in the spring of 2017 and germinated in June 2017. Seedlings were transplanted to a greenhouse in July 2017, hardened off in a shade house in August 2017, and transplanted to the field in September 2017. 'UC Keystone' was one of 10,000 individual hybrid plants from 397 full-sib families that were grown in 2017-18). The population was visually phenotyped in the spring of 2018 to: (a) identify individuals with outstanding fruit size, firmness, symmetry, color, gloss, and visual appeal; (b) eliminate individuals with fruit defects and deformities; (c) estimate marketable fruit yields; (d) identify putative photoperiod insensitive individuals; (e) assess stolon proliferation (runner production) and plant architecture; and (f) select individuals for clonal multiplication and further testing. Ninety-four individuals from the 2017-18 selection cycle were selected for on-farm advanced testing (Phase I, II, and III) in day-neutral production environments, from Nipomo in southern California to Prunedale in northern California. Disease resistance of the selections was tested in Davis, California.

'UC Keystone' differs from the closest comparison varieties as follows: Parent 'UCD Moxie' has a "reduced runnering" phenotype and produces fewer runners than 'UC Keystone'. 'UC Keystone' has improved tolerance to *Macrophomina* compared to 'UCD Moxie', which is susceptible. 'UC Keystone' also has moderate resistance to Verticillium wilt compared to parent 'UCD Warrior', which is moderately susceptible. 'UC Keystone' is less compact and has shorter flower trusses than related variety 'UC Golden Gate' and produces higher yields of fruit in the late season compared to 'UC Golden Gate', which produces more fruit early in the season. Further comparison varieties 'Monterey' (U.S. Plant Pat. No. 19,767), 'UCD Royal Royce' (U.S. Plant Pat. No. 32,952) and 'UCD Valiant' (U.S. Plant Pat. No. 32,984) employed in comparative field trials described herein are susceptible to Fusarium wilt, in contrast to 'UC Keystone'.

'UC Keystone' was genotyped with a 50,000-SNP array (Hardigan et. al., *Frontiers in Plant Science* 10:1789, 2020; Hardigan et al., *Mol. Biol. Evol.* 38:2285-2305, 2021) that included 72 cultivars owned by the University of California and 300 publicly available cultivars not owned by the University of California. After quality- and LD-pruning, 31,212 SNP markers with well-separated codominant genotypic clusters were selected for further analysis. These analyses confirmed that 'UC Keystone' is genetically distinct from its parent varieties, related variety 'UC Golden Gate', and comparison varieties 'Monterey', 'UCD Royal Royce', and 'UCD Valiant', as well as all of the other cultivars evaluated.

BRIEF DESCRIPTION OF THE DRAWINGS

The colors in the photograph are depicted as nearly true as is reasonably possible to obtain in color reproductions of this type.

DETAILED DESCRIPTION

Botanical Description

Figure 1:
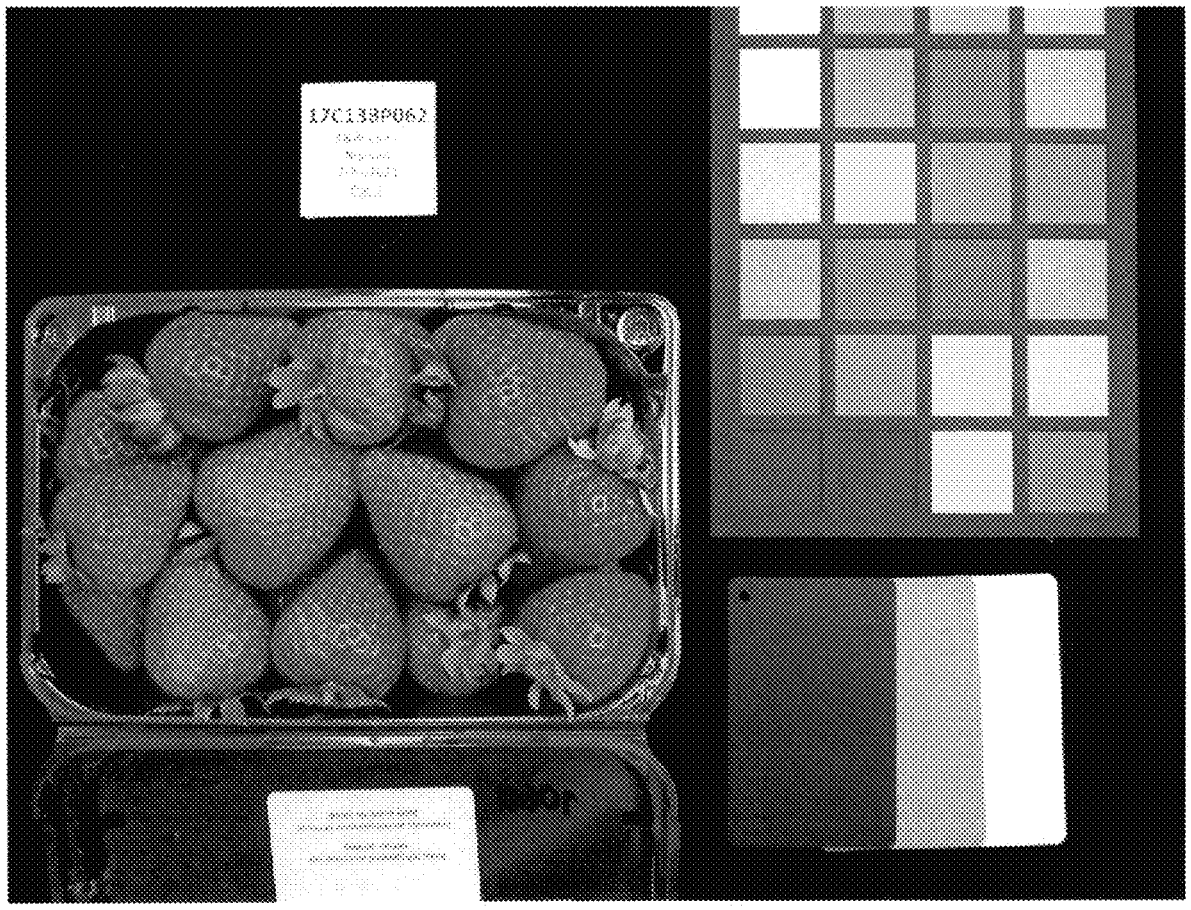
FIG. 1 depicts fruit of 'UC Keystone'.
Figure 2:
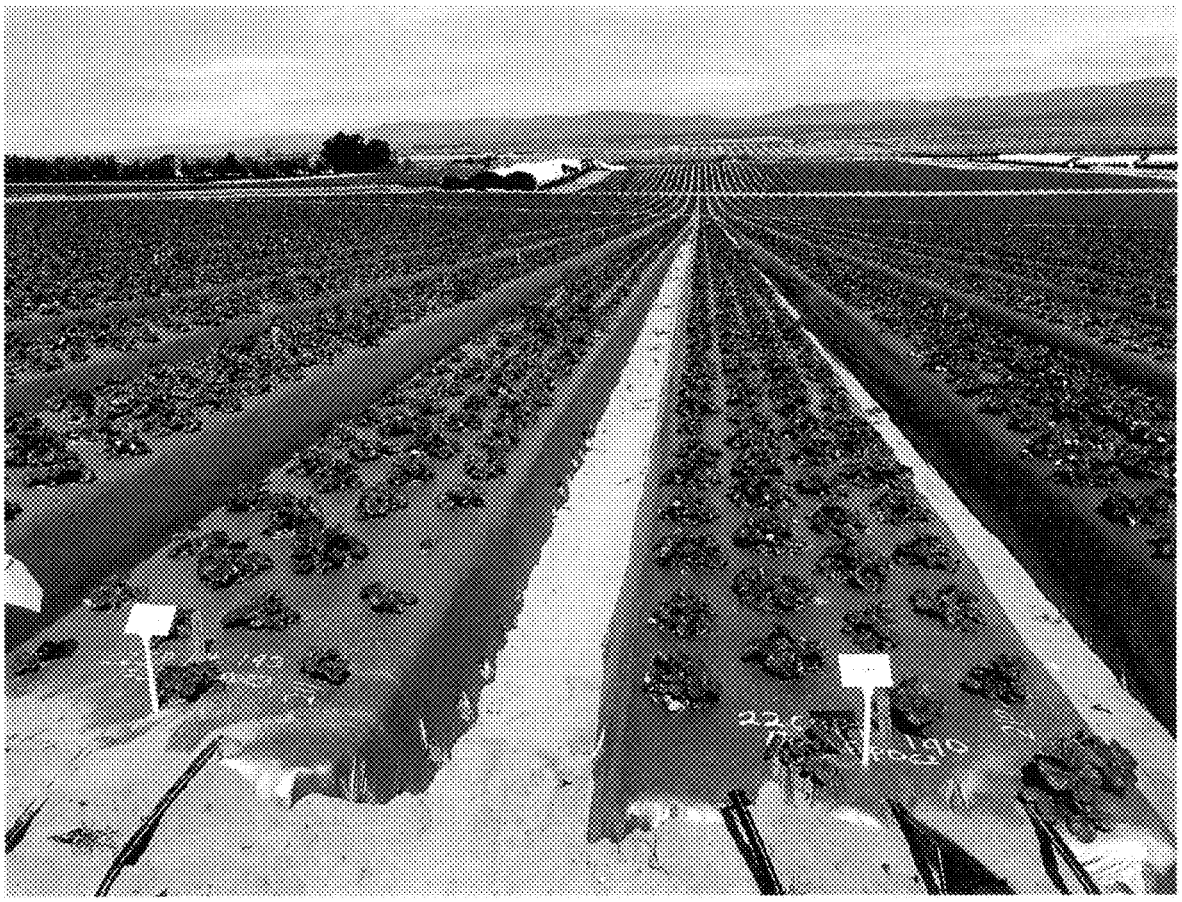
FIG. 2 shows 5-month old 'UC Keystone' plants.

Botanical descriptors of 'UC Keystone' are provided in Table 1. The descriptors were collected in the spring and summer of 2022 from plants grown in Santa Maria, California. Plants evaluated in the spring were 6 months old. Plants evaluated in the summer were 8 months old. Colors are designated with reference to The Royal Horticultural Society (R.H.S.) Colour Chart, Sixth Edition, 2015. The characteristics of 'UC Keystone' may vary in detail, depending upon environmental factors and culture conditions.

TABLE 1

[a]Mean values were estimated from nine samples per trait.

| Category | Trait | Unit | Range (Mean[a]) or Color (RHS Colour Designation) |
|---|---|---|---|
| Foliar | Plant height | mm | 300-360(328) |
| Foliar | Plant spread | mm | 520-620(566) |
| Foliar | Plant growth habit | | Semi-upright |
| Foliar | Position of the inflorescence in relation to foliage | | Above |
| Foliar | Mid-tier leaflet length | mm | 90-120(102) |
| Foliar | Mid-tier leaflet width | mm | 110-140(129) |
| Foliar | Petiole length | mm | 230-290(250) |
| Foliar | Stipule core color | color code | Moderate Yellow Green (146 C) |
| Foliar | Stipule margin color | color code | Moderate Yellow Green (146 A) |
| Foliar | Stolons/nursery mother plant | count | 10-12(11.0) |
| Foliar | Stolon color | color code | Brilliant Yellow Green (150 C) |
| Foliar | Leaf color, adaxial | color code | Moderate Olive Green (147 A) |

TABLE 1-continued

[a]Mean values were estimated from nine samples per trait.

| Category | Trait | Unit | Range (Mean[a]) or Color (RHS Colour Designation) |
|---|---|---|---|
| Foliar | Leaf color, abaxial | color code | Moderate Yellow Green (147 B) |
| Foliar | Leaf, blistering | | Medium |
| Foliar | Leaf, glossiness | | Medium |
| Foliar | Leaf, shape of the base of terminal leaflet | | Obtuse |
| Flower | Petal, arrangement of petals | | Overlapping |
| Flower | Petal number | count | 5-6(5) |
| Flower | Petal length | mm | 10-15(12) |
| Flower | Petal width | mm | 10-15(12) |
| Flower | Calyx diameter | mm | 25-40(35) |
| Flower | Corolla diameter | mm | 19-27(21) |
| Flower | Calyx, size in relation to corolla | | Larger |
| Flower | Flower, Stamen | | Present |
| Flower | Sepal number | count | 10-15(11) |
| Flower | Calyx Color | color code | Moderate Olive Green (137 A) |
| Flower | Upper Petal Color | color code | White (NN155 D) |
| Flower | Lower Petal Color | color code | White (NN155 D) |
| Flower | Stamen number | count | 22-32(27) |
| Fruit | Achene Color | color code | Greenish Brilliant Yellow (4 A) |
| Fruit | Position of achenes | | Below Surface |
| Fruit | Fruit length | mm | 43-56(50) |
| Fruit | Fruit width | mm | 30-38(34) |
| Fruit | Shape | | Conical |
| Fruit | Size of hollow core | mm | 0-10(6) |
| Fruit | External Fruit (exterior) color | color code | Vivid Red (44 A) |
| Fruit | Fruit flesh color | color code | Vivid Reddish Orange (33 A) |
| Fruit | Fruit core color | color code | Moderate Reddish Orange (35 A&B) |
| Fruit | Fruit size | g/fruit | 22-30(26) |

The time of the beginning of flowering is late February, 4 months post-planting.

*Fusarium* Resistance

Marker-assisted selection was employed to identify individuals predicted to be heterozygous or homozygous for the dominant (favorable) alleles for a Fusarium wilt resistance locus (FW1) and the PERPETUAL FLOWERING (PF) locus. The genotypes predicted by PF- and FW-linked SNPs for 'UC Keystone' were PFpf and FW1fw1. The predicted genotypes were confirmed with a 50,000 Aximo SNP array (Hardigan et al, 2020).

The dominant FW1 allele confers resistance to *Fusarium* wilt race 1, cause by *Fusarium oxysporum* f.sp. *fragariae*. *Fusarium* resistance was further tested by three years of replicated testing of bare-root plants artificially inoculated with AMP132, a race 1 isolate of the pathogen. The resistance of 'UC Keystone' to *Fusarium* wilt was compared to that of 'UC Golden Gate', 'San Andreas' (U.S. Plant Pat. No. 19,975), which is heterozygous FW1fw1 *Fusarium* wilt-resistant; and to susceptible (homozygous recessive (fw1fw1)) varieties 'Monterey', 'UCD Royal Royce', and 'UCD Valiant'. 'UC Keystone', 'UC Golden Gate', and 'San Andreas' were symptomless in these *Fusarium* wilt screening trials over three years (Table 2) with the mean disease scores in the highly resistant range and were not significantly different. The mean disease scores for 'Monterey', 'UCD Royal Royce', and 'UCD Valiant' were significantly greater than for 'UC Keystone' (ordinal scores increase as disease symptoms increase).

'UC Keystone' resistance to *Verticillium* wilt and *Phytophthora* crown rot (PhCR) was also evaluated (see, also Table 3) in comparison to 'UC Golden Gate', 'Monterey', 'UCD Royal Royce', and 'UCD Valiant'. 'UC Keystone' and 'UC Golden Gate' are moderately resistant to these diseases. Their resistance phenotypes are not significantly different from those of 'San Andreas' and 'Monterey', and other commercially important cultivars.

TABLE 2

Across-year estimated-marginal means (EMMs)[a] for *Fusarium* wilt, *Verticillium* wilt, and *Phytophthora* crown rot (PhCR) resistance scores[b] for 'UC Keystone', 'UC Golden Gate', 'UCD Valiant', 'UCD Royal Royce', 'San Andreas', and 'Monterey' observed in 2019-20, 2020-21, and 2021-22 disease resistance screening trials in Davis, CA.

| Disease[c] | | Test Cultivar Check Cultivar EMM[d] | Check Cultivar EMM | t[e] | p-value[f] |
|---|---|---|---|---|---|
| *Fusarium* Wilt | UCD Valiant | 1.25 | 2.88 | −3.86 | 0.0003 |
| | UCD Royal Royce | | 2.98 | −4.12 | 0.0001 |
| | San Andreas | | 1.15 | 0.19 | 0.85 |
| | Monterey | | 3.36 | −4.67 | <0.0001 |
| | UC Golden Gate | | 1.17 | 0.19 | 0.85 |
| *Verticillium* Wilt | UCD Valiant | 2.12 | 1.93 | 0.43 | 0.67 |
| | UCD Royal Royce | | 2.31 | −0.44 | 0.66 |
| | San Andreas | | 1.29 | 1.19 | 0.24 |
| | Monterey | | 2.36 | −0.46 | 0.64 |
| | UC Golden Gate | | 1.97 | 0.34 | 0.74 |
| *Phytophthora* Crown Rot | UCD Valiant | 2.44 | 2.25 | 0.35 | 0.73 |
| | UCD Royal Royce | | 2.33 | 0.21 | 0.84 |
| | San Andreas | | 1.83 | 0.85 | 0.40 |
| | Monterey | | 3.07 | −0.92 | 0.36 |
| | UC Golden Gate | | 2.25 | 0.34 | 0.73 |

[a]EMMs were estimated from four replications/entry/year over three years (12 observations/entry), except for *Fusarium*, where additional screening in 2022 resulted in 24 observations/entry.
[b]The ordinal symptom rating scales were identical for each disease: 1 = highly resistant, 2 = moderately resistant, 3 = moderately susceptible, 4 = susceptible, and 5 = highly susceptible.
[c]The fungal pathogens causing these diseases are *Fusarium oxysporum* f. sp. *fragariae* (*Fusarium* wilt), *Verticillium dahliae* (*Verticillium* wilt), *Phytophthora cactorum* (*Phytophthora* crown rot).
[d]The 'test' cultivars were 'UC Keystone' (shown in the upper half of the table) and 'UC Golden Gate' (shown in the lower half of the table).
[e]t-statistics for linear contrasts ($EMM_1$-$EMM_2$) between the EMMs for 'UC Keystone' or 'UC Golden Gate' and check cultivars.
[f]The probability of a greater t-statistic by chance for tests of the null hypothesis of no difference between EMMs ($H_0$: $EMM_1 = EMM_2$).

Photoperiod Insensitive Phenotype

The dominant PF allele is necessary for photoperiod insensitive flower in cultivated strawberry. The predicted photoperiod insensitive phenotype of 'UC Keystone' was confirmed through three years of on-farm testing in Sana Maria, California and Prunedale, California. 'UC Keystone' consistently flowered and fruited throughout the commercial day-neutral growing seasons in Nipomo (35.0N) and Prunedale (36.8N) where daylengths ranged from 9.8 to 14.7 hours.

Field Evaluations

Three seasons of advanced testing of selected day-neutral hybrids originating from the 2017-18 breeding cycle, starting with ninety-four in 2018-19 and finishing with six in 2021-22, one of which was 'UC Keystone', were completed. Comparison cultivars were 'UC Golden Gate', 'Monterey', 'UCD Royal Royce', and 'UCD Valiant'.

Clones (asexually propagated bare-root plants) for the first year of testing (Phase I in 2018-19) were produced in Winters, California. Clones for subsequent years of testing (Phase II in 2019-20 and 2020-21 and Phase III in 2021-22 and 2022-23) were produced in commercial high-elevation nurseries (Dorris, California) using standard production and propagation practices and post-harvest chilling treatments optimized for the day-neutral market segment. Clones were harvested in late October, trimmed, and directly planted in late October and early November of each year.

For on-farm yield trials, plants were grown in two 10-plant plots in Phase I and two 20-plant plots in Phase II yield trials, and two 500- or 1,000-plant strips in Phase III yield trials. The plots were arranged in randomized complete blocks experiment designs in commercial production fields. These experiments were grown using the management practices, bed configurations, plastic mulches, planting densities, planting dates, irrigation, fertilization, and pesticide application decisions and schedules, and harvest schedules of our cooperators.

Marketable fruit yield, count, and size were recorded at each harvest. Collection and analysis of 18,526 observations were employed for these traits to support statistical analyses.

Fruit Quality

Fruit from early and peak season harvests from every trial were performed to phenotype hybrids for firmness, total soluble solids (TSS=Brix), and titratable acidity (TA). The peak and late season fruit from four environments were stored at 4° C. and screened for post-harvest perishability over 14 days. These samples were phenotyped for weight, TSS, TA, firmness, gloss, and leakage at 0, 7, and 14 days post-harvest (DPH). Over three growing seasons, 2,273 phenotypic observations were collected for fruit quality traits at harvest to support statistical analyses and selection decisions.

Plants were assessed for flavor and aroma through informal hedonic testing in the field and laboratory by various individuals. Although specific volatile organic compounds (VOCs) known to affect aroma were not selected for, selection pressure for enhanced flavor and aroma was applied and VOC profiles were analyzed for 152 cultivars and other hybrids over two years of on-farm testing. 'UC Keystone' was among the hybrids phenotyped for VOC. These data were used to assess the effect of subjective olfactory and gustatory assessments on aroma profile changes. VOC analyses were performed using solid phase microextraction (SPME) gas chromatography-mass spectroscopy of fruit samples collected from early and peak season harvests over two years from on-farm yield trials in Santa Maria and Prunedale, California. Although at least 360 VOCs have been identified in developing strawberry receptacles, aroma and flavor are dominated by fewer than 10. Data for approximately 52 VOCs affecting aroma (58,488 phenotypic observations) were collected and analyzed to support statistical analyses. Data for three VOCs (γ-decalactone, mesifurane, and linalool) that are predicted to contribute towards the improved flavor of 'UC Keystone' and 'UC Golden Gate' are provided.

The fruit quality of 'UC Keystone' equal or exceeds the fruit quality and shelf life standards of long shelf life (LSL) cultivars designed for prolonged cold storage and long-distance shipping. Table 3 provides a comparison of the cumulative marketable fruit yields and other fruit traits.

TABLE 3

Across-environment estimated marginal means (EMMs) for cumulative marketable fruit yield and other fruit traits for 'UC Keystone' and comparison cultivars grown on commercial farms in Nipoomo and Prunedale, CA over three growing seasons (2019-20 to 2021-22)[a].

| Trait[a] | Comparison Cultivar | UC Keystone EMM | Comparison Cultivar EMM | t[b] | p-value[c] |
|---|---|---|---|---|---|
| Yield (lb/acre) | Monterey | 103,710 | 88,323 | 1.42 | 0.16 |
| | UCD Valiant | | 91,783 | 1.10 | 0.28 |
| | UCD Royal Royce | | 89,044 | 1.35 | 0.18 |
| | UC Golden Gate | | 95,730 | 0.73 | 0.47 |
| Size (g/fruit) | Monterey | 28.0 | 29.7 | −3.23 | 0.001 |
| | UCD Valiant | | 33.0 | −8.91 | <0.0001 |
| | UCD Royal Royce | | 28.8 | −1.39 | 0.16 |
| | UC Golden Gate | | 28.7 | −1.20 | 0.23 |
| Firmness (g-force) | Monterey | 260.6 | 239.1 | 1.96 | 0.05 |
| | UCD Valiant | | 297.1 | −2.93 | 0.005 |
| | UCD Royal Royce | | 349.9 | −7.18 | <0.0001 |
| | UC Golden Gate | | 303.7 | −3.25 | 0.002 |
| TSS (%) | Monterey | 8.29 | 8.89 | −4.19 | 0.0001 |
| | UCD Valiant | | 7.37 | 5.78 | <0.0001 |
| | UCD Royal Royce | | 7.57 | 4.55 | <0.0001 |
| | UC Golden Gate | | 7.84 | 2.59 | 0.01 |
| TA (%) | Monterey | 0.77 | 0.76 | −0.39 | 0.70 |
| | UCD Valiant | | 0.82 | −2.97 | 0.005 |
| | UCD Royal Royce | | 0.82 | −2.87 | 0.006 |
| | UC Golden Gate | | 0.85 | 4.21 | 0.0001 |
| TSS/TA | Monterey | 11.01 | 10.44 | −2.69 | 0.01 |
| | UCD Valiant | | 9.20 | 6.35 | <0.0001 |
| | UCD Royal Royce | | 9.55 | 5.12 | <0.0001 |
| | UC Golden Gate | | 9.45 | 5.19 | <0.0001 |

[a]Cumulative marketable fruit yields were estimated from fruit harvested on commercial schedules (once or twice weekly) over the entire day-neutral growing season on each farm. Fruit firmness, total soluble solids (TSS), and titratable acidity (TA) were measured from multiple fruit/replication sampled from two harvests/trial. EMMs and test statistics were estimated from the phenotypes of fruit harvested from two 24-plant plots/entry/environment.
[b]t-statistics for linear contrasts ($EMM_1$-$EMM_2$) between 'UC Keystone' and check cultivar EMMs.
[c]The probability of a greater t-statistic by chance for tests of the null hypothesis of no difference between EMMs ($H_0$: $EMM_1 = EMM_2$).

'UC Keystone' produced large fruit (28.0 to 28.7 g/fruit) in the on-farm trials (Table 3). Their fruit weights were in the normal range for mass-produced day-neutral cultivars in California and above the market critical threshold needed for cost-effective hand harvest (labor costs increase as fruit size decreases).

'UC Golden Gate' fruit were significantly firmer (303.7 g-force) than 'UC Keystone' (260.6 g-force; p=0.0002) and 'Monterey' (239.1 g-force; p<0.0001). The firmness of these cultivars exceeded the threshold (>230 g-force) necessary for minimizing harvest and post-harvest losses and delivering a high quality product to markets over long distances.

The sweetness and sourness profiles of 'UC Keystone' and 'UC Golden Gate' are slightly different. Total soluble solids (TSS) were slightly greater for 'UC Keystone' (8.33) than 'UC Golden Gate' (7.85; p=0.008), whereas titratable acidity (TA) was greater for 'UC Golden Gate' (0.83) than 'UC Keystone' (0.74; p=0.0003). The TSS/TA ratio (a measure of perceived sweetness) was significantly greater for 'UC Keystone' (11.66) than 'UC Golden Gate' (9.86; p=0.0001) and non-significantly greater than 'Monterey' (10.44; p=0.01), whereas the TSS/TA ratio for 'UC Golden Gate' was significantly lower than 'Monterey' (p<0.0001). Hence, the sweetness and perceived sweetness ratings for 'UC Keystone' and 'Monterey' were virtually identical and greater than that of 'UC Golden Gate'.

'UC Keystone' and 'UC Golden Gate' were identified to have improved aroma from subjective olfactory and gustatory assessments of fruit. Solid phase microextraction (SPME) GC-MS analyses of volatile organic compounds (Table 4) suggested that part of the improved flavor of 'UC Keystone' and 'UC Golden Gate' can be attributed to an increase in γ-decalactone (5-hexyloxolan-2-one), the most abundant lactone found in strawberry. This VOC, which imparts an intense-peach flavor, is abundant in 'Albion' (U.S. Plant Pat. No. 16,228) and absent in 'Monterey'.

TABLE 4

Across-year estimated-marginal means (EMMs)[a] for γ-decalactone, mesifurane, and linalool concentrations[a] in ripe fruit of 'UC Keystone', 'UC Golden Gate', and comparison cultivars harvested in 2020-21 and 2021-22 from on-farm yield trials in Nipomo, CA.

| Cultivar | γ-decalactone EMM | mesifurane EMM | linalool EMM |
|---|---|---|---|
| Monterey | 0 | 1,025,275 | 58,682 |
| UCD Royal Royce | 7,253 | 247,148 | 0 |
| UCD Valiant | 14,406 | 213,015 | 1,374 |
| UC Keystone | 34,740 | 156,584 | 20,783 |
| UC Golden Gate | 7,273 | 241,300 | 6,265 |
| Albion | 132,592 | 991,288 | 17,942 |
| LSD[b] | 109,763 | 146,678 | 26,860 |

[a]EMMs were estimated from fruit sampled from two 20- or 40-plant plots/entry/year. The relative concentrations of volatile organic compounds (ng/g dry weight) were estimated from the raw solid phase microextraction (SPME) GC-MS data (peak area in counts) and normalized samples.
[b]Least significant differences are shown for a false-positive probability of p = 0.05.

'UC Keystone' and 'UC Golden Gate' meet or exceed the shelf life requirements for mass-produced cultivars developed for cold storage and long distance shipping in California. Minimal declines were observed in the deterioration of fruit firmness and other fruit quality traits over 14 days of post-harvest cold storage using fruit sampled from peak and late season harvests No statistically significant differences for fruit weight, TSS, TA, or leakage between 'UC Keystone' and 'UC Golden Gate' and comparison cultivars were observed.

Fruit Production Characteristics—Field Trials

The number of harvests ranged from 40 to 61 in each trial to assess 'UC Keystone' fruit production in comparison to that of 'UC Golden Gate' 'Monterey', 'UCD Royal Royce', and 'UCD Valiant'. Marketable fruit yield, count, and size were recorded at each harvest. Collection and analysis of 18,526 observations was performed for these traits to support statistical analyses.

Statistics are shown for linear contrasts between the estimated marginal means (EMMs) for 'UC Keystone', 'UC Golden Gate' , and comparison cultivars across environment (2 locations 3 years) and for individual environments to highlight variation in planting dates, the number of harvests, harvest ranges, and production practices (Table 5). EMMs were estimated from two 20-plant plots (replications)/entry/environment in 2020 and 2021 and two 540-plant plots in 2022.

| Location | Season | Comparison Cultivar | UC Keystone EMM (lb/a) | Compare Cultivar EMM (lb/a) |
|---|---|---|---|---|
| Nipomo | 2019-20 | Monterey | 88,028 | 64,797 |
| | | UC Royal Royce | | 79,625 |
| | | UC Valiant | | 90,853 |
| | | UC Golden Gate | | 82,971 |
| Prunedale | 2019-20 | Monterey | 103,149 | 73,300 |
| | | UC Royal Royce | | 101,146 |
| | | UC Valiant | | 81,841 |
| | | UC Golden Gate | | 103,065 |
| Nipomo | 2020-21 | Monterey | 99,214 | 70,682 |
| | | UC Royal Royce | | 93,142 |
| | | UC Valiant | | 107,279 |
| | | UC Golden Gate | | 99,935 |
| Prunedale | 2020-21 | Monterey | 115,908 | 97,546 |
| | | UC Royal Royce | | 128,842 |
| | | UC Valiant | | 119,684 |
| | | UC Golden Gate | | 123,669 |
| Nipomo | 2021-22 | Monterey | 56,691 | 69,976 |
| | | UC Royal Royce | | 39,241 |
| | | UC Valiant | | 57,602 |
| | | UC Golden Gate | | 59,740 |
| Prunedale | 2021-22 | Monterey | 158,914 | 152,127 |
| | | UC Royal Royce | | 92,924 |
| | | UC Valiant | | 93,437 |
| | | UC Golden Gate | | 104,999 |

-continued

| | Location | Yield Change (%)[b] | t[c] | p-value[d] |
|---|---|---|---|---|
| | Nipomo | 35.9 | 3.70 | 0.004 |
| | | 10.6 | 1.03 | 0.33 |
| | | −3.1 | −0.45 | 0.66 |
| | | 6.1 | 0.84 | 0.42 |
| | Prunedale | 40.7 | 5.56 | 0.0002 |
| | | 2.0 | 0.37 | 0.72 |
| | | 26.0 | 3.97 | 0.002 |
| | | 0.1 | 0.02 | 0.99 |
| | Nipomo | 40.4 | 3.16 | 0.01 |
| | | 6.5 | 0.67 | 0.52 |
| | | −7.5 | −0.89 | 0.39 |
| | | −0.7 | −0.08 | 0.94 |
| | Prunedale | 18.8 | 2.92 | 0.01 |
| | | −10.0 | −2.05 | 0.06 |
| | | −3.2 | −0.60 | 0.56 |
| | | −6.3 | −1.23 | 0.24 |
| | Nipomo | −19.0 | −5.17 | <0.0001 |
| | | 44.5 | 5.54 | <0.0001 |
| | | −1.6 | −0.29 | 0.78 |
| | | −5.1 | −0.97 | 0.34 |
| | Prunedale | 4.5 | 1.25 | 0.23 |
| | | 71.0 | 9.89 | <0.0001 |
| | | 9.8 | 70.1 | <0.0001 |
| | | 51.3 | 8.08 | <0.0001 |

[a]Linear contrasts between estimated marginal means (EMMs) for 'UC Keystone' and comparison cultivars were estimated for each environment. EMMs were estimated from two 20-or 40-plant plots/entry within each environment. Cumulative marketable fruit yields were estimated from fruit harvested on commercial schedules (once or twice weekly) over the entire day-neutral growing season on each farm.

[b]The yield change percentage was estimated by $(EMM_1 - EMM_2)/EMM_2 \times 100$.

[c]t-statistics for linear contrasts $(EMM_1 - EMM_2)$ between the EMMs for 'UC Keystone' and comparison cultivars.

[d]The probability of a greater t-statistic by chance for tests of the null hypothesis of no difference between EMMs ($H_0$: $EMM_1 = EMM_2$).

'UC Keystone' and 'UC Golden Gate' were the highest yielding cultivars in these trials. When averaged across environments, however, the yields of 'UC Keystone', 'UC Golden Gate', and the three comparison cultivars were not statistically different. Thus, 'UC Keystone' has yields at least equal to the *Fusarium* wilt-susceptible comparison cultivars.

The cumulative marketable fruit yields of 'UC Keystone' were 6,787 to 29,849 lb/a greater than 'Monterey' in five environments and 13,285 lb/a lb/a less than 'Monterey' in one environment (Nipomo 2021-22) (Table 5).

The cumulative marketable yield plots for each environment highlight the differences among cultivars and growing seasons. The yields of 'Monterey' were below and separated from 'UC Keystone', 'UC Golden Gate', and the other comparison cultivars in the first two growing seasons. Yields dropped in the last growing season (2021-22) in Nipomo especially compared to previous years, with less separation among cultivars.

The cumulative marketable fruit yields of 'UC Keystone' and 'UC Golden Gate' were not significantly different in five of six test environments or across environments (Tables 3 and 5). The yield of 'UC Keystone' was significantly greater than 'UC Golden Gate' in one environment (Prunedale 2021-2022). The reasons for yield decreases for 'UC Golden Gate', 'UCD Royal Royce', and 'UCD Valiant' in the 2021-22 Prunedale trial were not clear. The affected plants ultimately recovered, however, and produced an abundance of fruit later in the season.

'UC Keystone' is thus a highly productive *Fusarium* wilt resistant cultivar for the day-neutral segment that meets or exceeds the shelf life, flavor, and fruit quality characteristics of 'Monterey'.

What is claimed is:

1. A new and distinct cultivar of strawberry plant named 'UC Keystone', substantially as described and illustrated herein.

* * * * *